(12) United States Patent
Kamiyama (10) Patent No.: US 6,245,019 B1
(45) Date of Patent: Jun. 12, 2001

(54) ULTRASONIC DIAGNOSTIC APPARATUS (75) Inventor: Naohisa Kamiyama, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/302,260

(22) Filed: Apr. 30, 1999

(30) Foreign Application Priority Data

May 11, 1998 (JP) .................................................. 10-127442

(51) Int. Cl.[7] ........................................................ A61B 8/14
(52) U.S. Cl. .......................................................... 600/458
(58) Field of Search .................................. 600/443, 440, 600/441, 447, 458; 367/7

(56) References Cited

U.S. PATENT DOCUMENTS

| | | |
|---|---|---|
| 5,456,257 | 10/1995 | Johnson et al. . |
| 5,560,364 | 10/1996 | Porter . |
| 5,685,310 | 11/1997 | Porter . |
| 5,694,937 | 12/1997 | Kamiyama . |
| 5,735,281 | 4/1998 | Rafter et al. . |
| 5,740,807 | 4/1998 | Porter . |
| 5,833,613 | * 11/1998 | Averkiou et al. ..................... 600/440 |
| 5,833,615 | * 11/1998 | Wu et al. ............................. 600/458 |
| 5,860,931 | * 1/1999 | Chandler ............................. 600/458 |
| 5,944,666 | * 8/1999 | Hossack et al. ..................... 600/458 |
| 5,947,904 | * 9/1999 | Hossack et al. ..................... 600/458 |

* cited by examiner

*Primary Examiner*—Marvin M. Lateef
*Assistant Examiner*—Ali M. Imam
(74) *Attorney, Agent, or Firm*—Oblon, Spivak, McClelland, Maier & Neustadt, P.C.

(57) ABSTRACT

An ultrasonic diagnostic apparatus includes an ultrasound probe, a transmitting device, a receiving device, a transmission control circuit, and an image generating unit. The transmission control circuit controls the transmitting device, so that an imaging region of a subject is scanned throughout with ultrasound during a scanning operation. The scanning operation is repeated, and ultrasound for collapsing microbubbles administered to the subject is transmitted in an interval between scanning operations. In a region where the ultrasound for collapsing micro-bubbles is transmitted, a greater number of micro-bubbles collapse than in the other region where the ultrasound for collapsing micro-bubbles is not transmitted. Accordingly, the contrast effect is partially reduced in the imaging region. Therefore, image data has a portion of a higher contrast effect and a portion of a lower contrast effect.

19 Claims, 6 Drawing Sheets

ULTRASONIC DIAGNOSTIC APPARATUS

BACKGROUND OF THE INVENTION

The present invention relates to an ultrasonic diagnostic apparatus for imaging a contrast echo from an ultrasound contrast medium to observe and quantify the bloodstream movement and the circulation movement of the blood on the internal organs parenchyma level by detecting perfusion.

Ultrasound is applied to various kinds of medical apparatuses, mainly an ultrasonic diagnostic apparatus for obtaining a tomogram of tissue of soft parts of a living body by means of the ultrasonic pulse reflection. The ultrasonic diagnostic apparatus obtains and displays a tomogram of tissue by means of a non-invasive examination method. The apparatus has the following advantages which cannot be obtained by the other kinds of diagnostic apparatus, such as X-ray diagnostic apparatus, X-ray computed tomographs, magnetic resonance imaging apparatuses (MRIs) and nuclear medical diagnostic apparatuses. The ultrasonic diagnostic apparatus can accomplish real-time display.

It is compact and inexpensive. It is improved in safety, since the subject is not exposed to X-ray or the like. Further, it can perform bloodstream imaging by the Doppler ultrasonography. For this reason, ultrasonic diagnosis is widely employed in the field of the heart, the abdominal organs, the mammary gland, the urinary organs, and obstetrics and gynecology. In particular, heartbeat or movement of a fetus can be display in real time by a simple operation of only applying an ultrasound probe to the body surface. In addition, since the apparatus is safe, examination can be repeated many times. Moreover, the apparatus can be easily moved to a bedside, so that examination can be carried out there.

(Contrast Medium)

To examine the heart or the abdominal organs using the ultrasonic diagnostic apparatus described above, injection of an ultrasound contrast medium through a vein and evaluation of the bloodstream movement by observing spread of the contrast medium have been put to practice. Since the intravenous injection of a contrast medium is less invasive than arteriographic echo using a catheter, it is considered that the diagnosis by means of the above method of evaluating bloodstream movement will be in common use.

Micro-bubbles, serving as reflectors having high reflectivity, are generally used as a contrast medium. The contrast effect of micro-bubbles is controllable, depending on the amount of injection and the concentration of the bubbles. However, since they are broken when irradiated with ultrasound, the contrast effect is maintained only for a short period of time.

Considering the site of a subject in a clinical situation, a contrast medium is supplied by the bloodstream continuously to the region of concern. Therefore, even if the micro-bubbles in the region of interest are collapsed by one irradiation of ultrasound, if new micro-bubbles are supplied to the region of interest before the next transmission of ultrasound, the contrast effect can be maintained. However, since ultrasound is generally transmitted several thousands of times a second, and the rate of the bloodstream is low in the internal organs parenchyma or a comparatively thin vessel, it is expected that there is no time for a fresh contrast medium to flow in and the contrast effect is reduced instantaneously.

The most basic diagnosis using a contrast medium is performed by detecting whether there is a contrast effect (increase in brightness) obtained by the contrast medium, thereby detecting whether there is a bloodstream in the diagnosis site. An improved diagnosis is carried out by observing a change with time of spatial distribution of a contrast medium in the diagnosis site in view of a spread of a change in brightness and an increase in brightness. It is also carried out by obtaining a time between the injection of the contrast medium and the arrival thereof to the region of interest (ROI), a change in time (TIC: Time Intensity Curve) of echo brightness in the ROI caused by the contrast medium, and the maximum brightness.

(Harmonic Imaging)

The contrast echo method using the contrast medium described above achieves more effective diagnosis by means of harmonic imaging. The harmonic imaging is a method for imaging a harmonic component generating from non-linear behavior caused by ultrasonic excitation, and separating it from a basic frequency component. In the living internal organs, since ultrasound has less tendency to exhibit non-linear behavior, the contrast medium can be observed at a satisfactory contrast ratio.

(Flash Echo Imaging)

As regards a method for positively utilizing the aforementioned phenomenon in which micro-bubbles are collapsed by ultrasonic irradiation, improvement of the brightness increasing effect is reported in "Flash Echo Imaging" (Reference document: 6795 Study of Flash Echo Imaging (1), Naohisa Kamiyama et al., 67th Meeting for Presenting Research Papers of Japanese Society of Ultrasonic Medicine and "Transient Response Imaging". In the method described in these documents, in principle, the conventional successive scan for scanning several frames per second is replaced by intermittent transmission for transmitting one frame in several seconds, thereby providing a time in which micro-bubbles are allowed to flow into the region of interest. When the micro-bubbles collect, ultrasound of a high sound pressure is transmitted and received, so that an echo signal of a high contrast can be obtained.

(Continuous Infusion)

A contrast medium can be administered into the body by various methods. Representative methods are: a bolus administration method for administering a contrast medium from an injector to a subject in a relatively short period of time; and a continuous infusion method for administering it little by little in a long period of time, for example, drip injection. The former is suitable for obtaining TIC, since it is relatively easy of administration and provides increased brightness at the peak when the contrast medium reaches the region of interest. However, the period, in which the contrast medium is maintained to a satisfactory concentration, is short. The latter method must be controlled by a special-purpose device, such as a constant infusion device; however, it is advantageous in that the concentration can be maintained for a satisfactory period of time. In the case of using an improved contrast medium, which has a sufficient contrast effect even if it is diluted, the latter method is more effective.

As described above, perfusion of internal organs has been able to be imaged by means of the intravenous contrast medium and the imaging method, such as harmonic imaging or flash echo imaging. However, it is known that the imaging of perfusion is not always possible but can hardly be detected because of the following problems.

The principle of harmonic imaging is to image only a harmonic component mainly resulting from non-linear reflection by the micro-bubbles in the contrast medium. The principle is based on the assumption that the level of a harmonic component resulting from non-linear transmission in tissue of the internal organs is much lower than that of a harmonic component resulting from micro-bubbles. However, the level of the harmonic component resulting from the internal organs is different from person to person. In many subjects, the level of the harmonic component resulting from the internal organs is comparatively high. In this case, as a result, even before administering the contrast medium, the echo brightness of the internal organs may be high. Particularly, in a portion where the bloodstream is very weak, after the contrast medium is administered, it is difficult to confirm whether the echo brightness is caused by the contrast medium.

In the experience of the inventor, when diagnosing the internal organs, the echo brightness in the case of cirrhosis of the liver or fatty liver is greatly different from those in the other cases. The same applies to detection of perfusion in the cardiac muscle. The cardiac muscle tissue also provides a number of harmonic components of comparatively high level in an echo signal. In particular, since an echo signal from the posterior wall of the cardiac muscle passes the ventriculus cordis, the waveform thereof is distorted by the blood (liquid) in that portion, resulting in increase in harmonic components. For this reason, even when a contrast medium is administered, the posterior wall of the cardiac muscle tends to provide high echo brightness.

BRIEF SUMMARY OF THE INVENTION

An object of the present invention is to provide an ultrasonic diagnostic apparatus which can effectively utilize the contrast echo method using a contrast medium (micro-bubbles).

According to the present invention, an imaging region in the subject is scanned throughout with ultrasound by controlling a transmitting device by means of a transmission control circuit during the scanning operation. The scanning operation is repeated, and in the interval between the operations, ultrasound for collapsing micro-bubbles administered to the subject is transmitted. In a region where the ultrasound for collapsing micro-bubbles is transmitted, a greater number of micro-bubbles collapse than in the other region where the ultrasound for collapsing micro-bubbles is not transmitted. Accordingly, the contrast effect is reduced in the former region as compared to the latter region. In other words, image data has a portion of a higher contrast effect and a portion of a lower contrast effect. The observer can compare the higher contrast effect portion and the lower contrast effect portion and confirm the contrast effect on one piece of image. As a result, the observer can recognize objectively, regardless of the level of intense reflection from tissue which considerably varies from person to person, whether the brightness is high because of the contrast effect or the intense reflection from tissue, i.e., the extent of the contrast effect.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

A preferred embodiment of the present invention will be described with reference to the drawings. The present invention relates to improvement of the contrast echo method for accentuating the bloodstream of the subject by means of a contrast medium. In the following description, it is assumed that the movement of the bloodstream flowing in the liver parenchyma or the cardiac muscle, to which the contrast echo is applied most frequently, is observed to identify an abnormal site.

Figure 1:
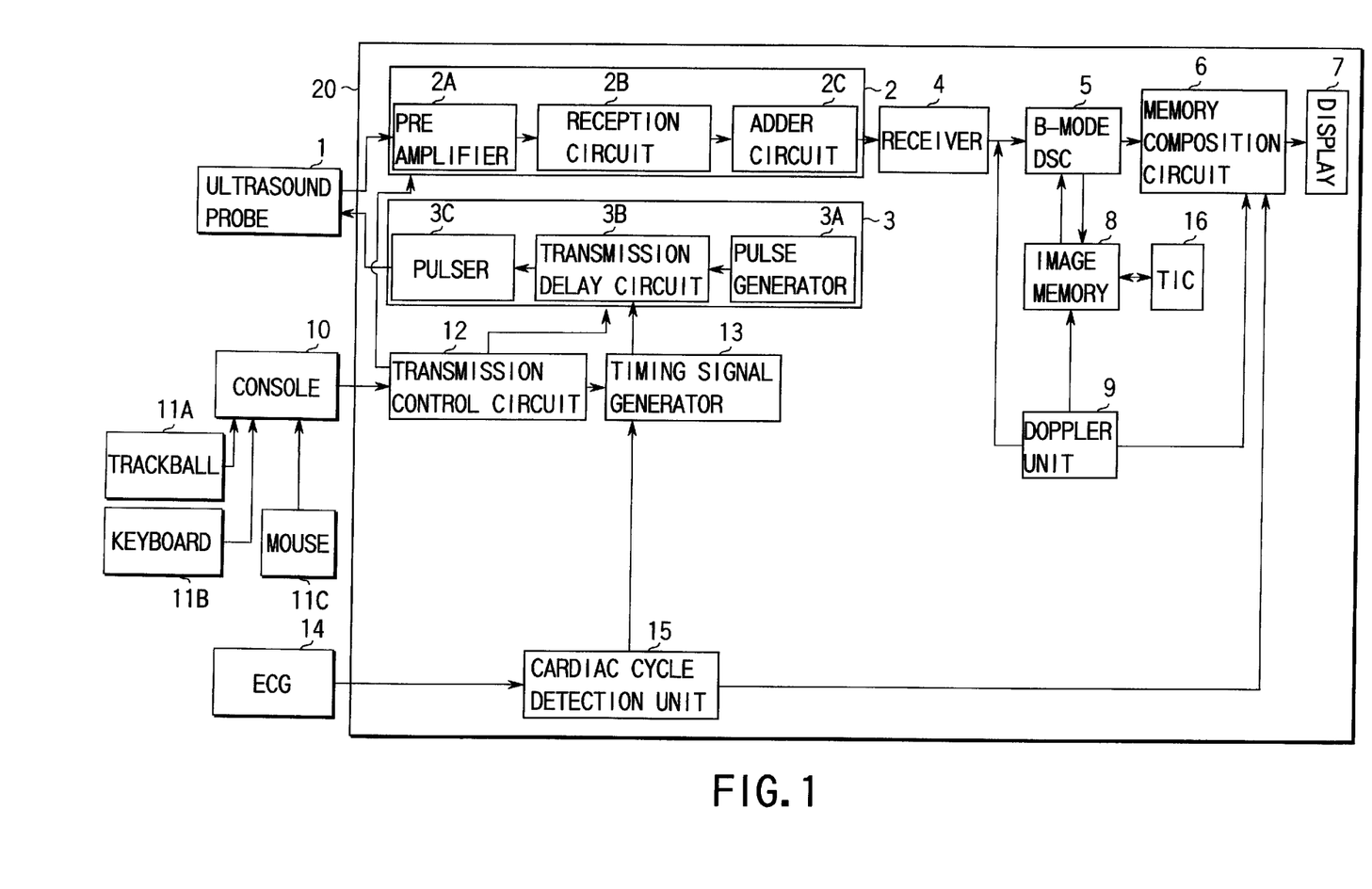
FIG. 1 is a block diagram showing a structure of an ultrasonic diagnostic apparatus according to a preferred embodiment of the present invention.

FIG. 1 is a block diagram showing a structure of an ultrasonic diagnostic apparatus according to the embodiment. A plurality of piezoelectric elements, for conversion between an ultrasonic signal and an electric signal, are arranged near the top end of an ultrasound probe 1. One piezoelectric element or a few adjacent elements constitute one channel.

The probe 1 is connected to an apparatus body 20. The apparatus body 20 is connected to a console 10 for interfacing the operator with the apparatus body 20 and input devices, such as a trackball 11A, a keyboard 11B, a mouse 11C, etc. According to the prior art, the input devices are used only to set transmission/reception conditions and a region of interest (ROI). However, according to this embodiment, they also have functions for setting or changing transmission conditions characteristic of this embodiment as will be described later.

The apparatus body 20 comprises a transmitting device 3, a receiving device 2, a receiver 4, a B-mode digital scan converter (DSC) 5, a memory composition circuit 6, a display 7, an image memory 8, a Doppler unit 9, a transmission control circuit 12, a timing signal generator 13 and a cardiac cycle detection unit 15. The cardiac cycle detection unit 15 is connected to an electrocardiograph (ECG) 14.

The transmitting device 3 includes a pulse generator 3A, a transmission delay circuit 3B and a pulser 3C. In general, transmission of a ultrasonic pulse is repeated in a cycle of 1/PRF in accordance with the pulse repetition frequency (PRF).

The transmission conditions of the transmitting device can be freely changed on the basis of a control signal output from the transmission control circuit 12. The transmission conditions are, for example, a transmission sound pressure (amplitude of a driving voltage), the number of simultaneously driven channels (transmission caliber), the transmission frequency of ultrasound (central frequency), and the burst wave number. The transmission timing signal generator 13 controls the transmission delay circuit 3B so that ultrasound can be received in accordance with the control signal from the transmission control circuit 12.

An echo transmitted from the probe 1 and reflected by a surface of discontinuity of acoustic impedance in the subject is received by the receiving device 2 through the same probe 1. The echo in each channel is amplified by a preamplifier 2A, given a delay time necessary to determine the reception directivity by the reception delay circuit 2B, and added by the adder 2C. The component reflected from the direction corresponding to the reception directivity is emphasized by the addition. A synthetic ultrasonic beam of transmission and reception is generated on the basis of the transmission directivity and the reception directivity.

The receiver 4 comprises a band-pass filter, a logarithmic amplifier, an envelope detecting circuit and an analog-to-digital converter (which are not shown), so that either a normal B-mode image or a harmonics image brightness-modulated by a harmonic component can be selectively generated. The pass band of the band-pass filter is controlled by a system controller (not shown), so that the component is substantially passed when the B-mode imaging is selected, whereas a harmonic component having a frequency a positive-integer number of times, for example, twice as high as that of the basic frequency, is mainly passed when the harmonic imaging is selected.

The receiver 4 outputs, as a one-dimensional signal, data relating to the B-mode image or the harmonics image in the order corresponding to the ultrasonic scanning procedure. The image data is rearranged (coordinate-converted) in the order of the video format by the B-mode digital scan converter 5 and transmitted to the memory composition circuit 6. The memory composition circuit 6 composes the image data and graphic data, such as set parameters, thereby generating a video signal corresponding to a screen actually displayed. The video signal is transmitted to the display 7 and displayed there.

In a color Doppler mode, the output signal from the receiving device 2 is transmitted to the Doppler unit 9. The Doppler unit 9 quadrature-detects the output signal and extracts a deviation frequency component deviated by the Doppler effect, i.e., a so-called Doppler signal. A clatter component of a comparatively low frequency, other than the high-frequency components relating to the object bloodstream, is removed from the Doppler signal, thereby extracting the high-frequency components. The extracted high-frequency components are subjected to autocorrelation, and the mean velocity, power and dispersion of each of a number of points on the basis of the results of autocorrelation are calculated. A color flow mapping image is produced from each or any combination of the mean velocity, power and dispersion. The color flow mapping image is also color-displayed in the display 7.

The image memory 8 stores image data in either or both of the formats before and after the coordinate conversion by means of the digital scan converter 5, so that the operator can freely call and reproduce the stored image at any time after the ultrasonic scanning.

The electrocardiograph 14 is used to obtain a cardiography waveform with electrodes adhered to suitable positions of the surface of the body. The cardiac cycle detection unit 15 transmits the obtained cardiography waveform along with the ultrasonic image to the memory composition circuit 6, so that they can be displayed in the display 7. It also outputs the cardiography waveform to the timing signal generator 13 as a trigger signal for obtaining an image of the heart collected in synchronism with the cardiographic waveform, i.e., a cardiographic synchronous image.

A transmission operation under control of the transmission control circuit 12 will now be described. The transmission operation is characteristic of the embodiment of this invention. It can be applied to either of the B mode and the harmonics mode. First and second ultrasounds are transmitted from the probe 1 under control of the transmission control circuit 12.

The first ultrasound is transmitted under the first transmission conditions (the kind of the ultrasound probe, the transmission sound pressure (the amplitude of the driving voltage of a piezoelectric element), the number of simultaneous driving channels (transmission caliber), the transmission frequency of ultrasound, and the burst wave number), which are suitable for imaging tissue of soft parts in the inside of the subject. The second ultrasound is transmitted under the second transmission conditions different from the first transmission conditions in order to enhance the efficiency of collapsing of the ultrasound contrast medium (micro-bubbles).

In the second transmission conditions, the transmission sound pressure is higher, the transmission caliber is wider, the transmission frequency is lower and/or the burst wave number is greater than those of the first transmission conditions, so that the micro-bubble collapsing efficiency can be enhanced.

Figure 2:
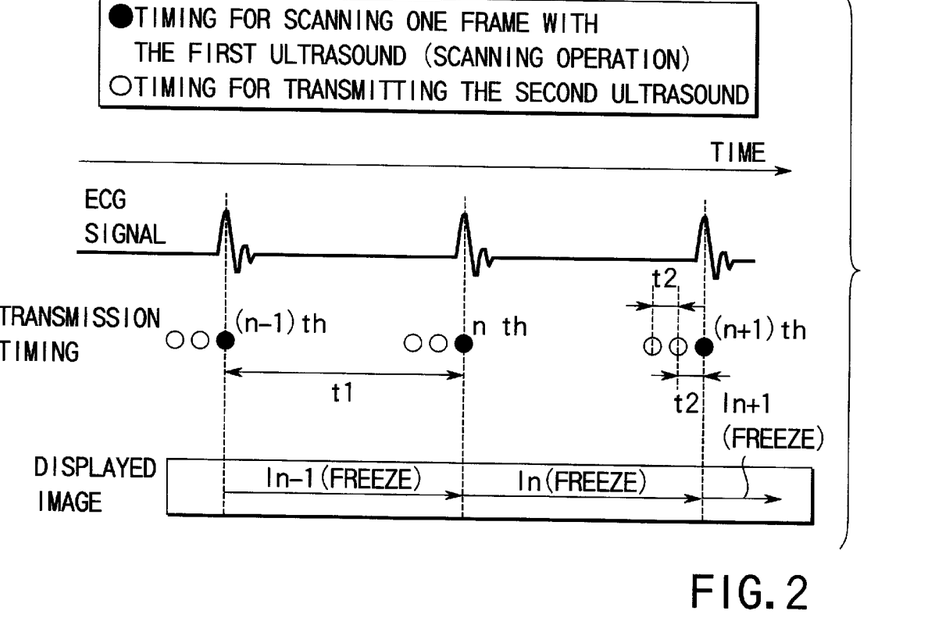
FIG. 2 is a diagram showing a transmission sequence of the embodiment.

FIG. 2 shows a transmission sequence of the transmission under control of the transmission control circuit 12. First, in the scanning operation for imaging, the first ultrasound under the first transmission conditions is transmitted to the subject, and a reflection wave from the subject is received. The directions of the transmission and the reception are shifted little by little, so that an imaging region (for example, slice) of the subject is scanned throughout. This scanning operation is repeated.

Figures 3A, 3B:
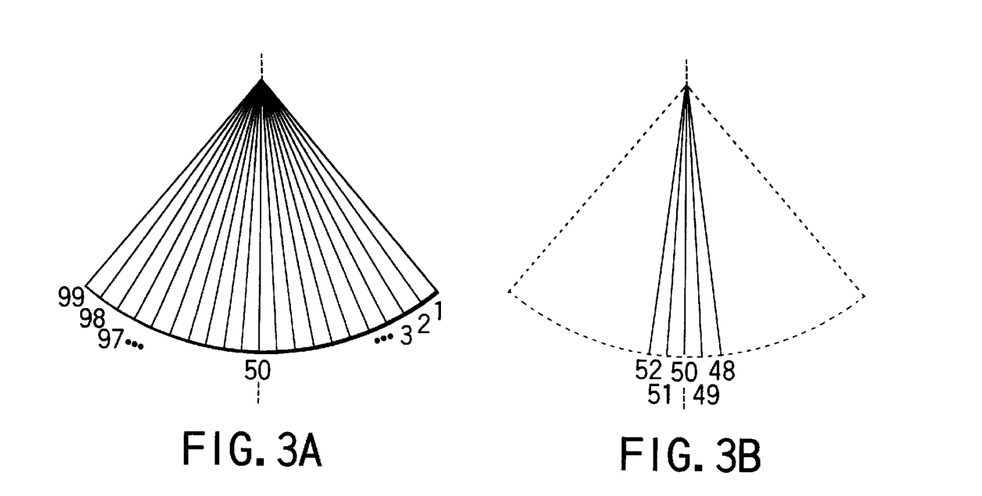
FIG. 3A is a diagram showing a scanning range of ultrasound under first transmission conditions for imaging in the embodiment.
FIG. 3B is a diagram showing a transmission range of ultrasound under second transmission conditions for collapsing micro-bubbles in the embodiment.

FIG. 3A shows the scanning range of the first ultrasound (ultrasound scanning lines 1 to 99). In this description, it is assumed that 99 ultrasound scanning lines constitute a piece of image (the 50th line is the center). For example, a time required for scanning a frame (a piece of image), i.e., a frame interval, is generally given by the number of ultrasound scanning lines/PRF in the B mode or the harmonics mode. The scanning of a frame by the first ultrasound is intermittently repeated in one cardiac cycle in synchronism with a cardiographic waveform. The scanning may be repeated intermittently in one cardiac cycle as shown in FIG. 2, but can be repeated in a longer cycle, for example, two or more cardiac cycles. Further, the scanning may be repeated in a fixed cycle, such as a second or two seconds, by means of an internal clock signal, independent of the cardiographic waveform. The operator can freely set and change the cycle of the scanning by operating the console 10.

The second ultrasound for collapsing micro-bubbles is transmitted to a part of the imaging region in an interval between scanning operations of intermittent scanning of a frame by the first ultrasound. FIG. 3B shows a portion where the second ultrasound is transmitted (ultrasound scanning lines 48 to 52). In the portion where the second ultrasound is transmitted, the delay data for transmitting the second ultrasound in an object direction may be constituted by original delay data more efficiently collapse the micro-bubbles. For example, it may be delay data having a high peak of the sound field in the ventriculus cordis. If part of the delay data of the first ultrasound is applied, the efficiency can be improved by the common data.

In this embodiment, the second ultrasounds of the respective ultrasonic scanning lines 48 to 52 are transmitted one by one, and the transmission of a set of the scanning lines is repeated twice. However, it may be repeated three times or more, or continuously transmitted in a scanning interval between scanning operations of adjacent frames.

The echo signal resulting from the transmission of the second ultrasound is not received by the apparatus, or even if the echo signal is received, an imaging process using the signal is not performed and the signal is discarded. Alternatively, even if a partial image of the ultrasound scanning lines 48 to 52 is formed by an imaging process, it is not displayed or recorded. Thus, the image obtained by the transmission of the second ultrasound is neither displayed or recorded, whereas the image obtained by the first ultrasound is displayed and recorded.

The transmission of the second ultrasound in a limited portion to collapse micro-bubbles in an interval between scanning operations for imaging, as described above, provides the following advantages. First, when the second ultrasound is transmitted, micro-bubbles in a region where a sound pressure is ensured are collapsed and almost entirely vanished. Thereafter, although fresh micro-bubbles flow in the region through the bloodstream, there is little time for the flow before the scanning with the first ultrasound starts. Therefore, substantially no micro-bubbles exist in the region.

Figure 4:
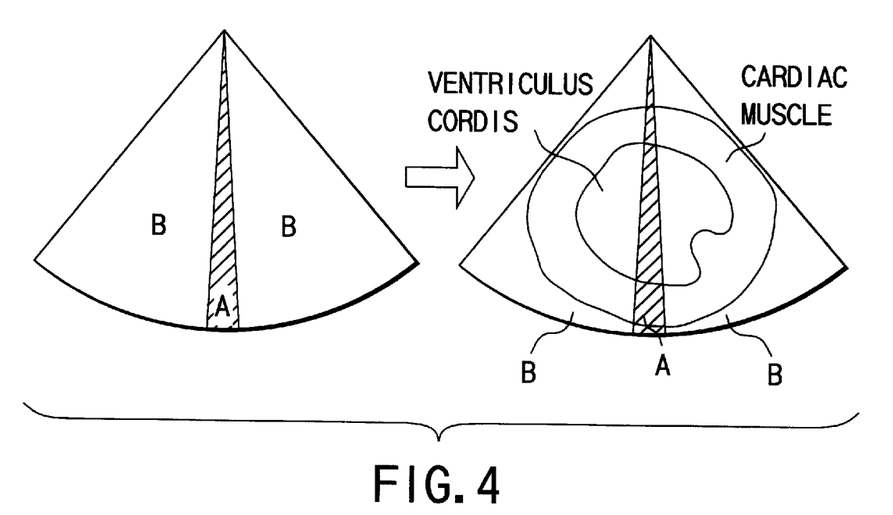
FIG. 4 is a diagram showing an example of an image obtained by the contrast echo method according to the embodiment.

Therefore, referring to FIG. 4, a sufficient amount of micro-bubbles exists and brightness is increased in a region B other than a region A in which the second ultrasound is transmitted. On the other hand, in the region A where the second ultrasound is transmitted, since there is substantially no micro-bubbles, the brightness is not increased. From the image as shown in FIG. 4, it is possible to observe the brightness of the brightness-increased region B with reference to that of the region A in which the brightness is not increased. Thus, it is possible to judge from only one image whether the harmonic component at harmonic imaging results from elastic scattering (non-linear behavior) of micro-bubbles or non-linear propagation in the internal organs. As a result, a very small bloodstream can be recognized effectively, when perfusion of internal organs is diagnosed.

In summary, it is possible to observe in one image both the portion which receives the brightness increasing effect (high contrast portion) and the portion which does not receive the effect (low contrast portion). Therefore, the extent of the brightness increase effect can be known by comparing the brightness of the two portions. Thus, the observer can realize whether the increase in brightness results from the contrast medium or the tissue, that is, to what extent the brightness is increased only by the contrast medium, regardless of the level of brightness which greatly varies from person to person.

Further, the operator can change in real time the range where the second ultrasound is transmitted by means of the trackball 11A, etc. Therefore, he or she can determine in real time whether a desired region is influenced by the second ultrasound, i.e., whether micro-bubbles exist in the region, while changing the ultrasound transmission lines for transmitting the second ultrasound, for example, from 48–52 to 50–55.

More specifically, if the brightness levels of the regions A and B in a portion near the boundary therebetween are both about 30, it is considered that only little amount of micro-bubbles are introduced in the heart, that is, the contrast increasing effect of the micro-bubbles is not exhibited very much. In this case, it is determined that the brightness in the region B results from the echo signal from the cardiac muscle. If the brightness of the region A is lower than that of the region B, for example, about 10, it is determined that the brightness in the region B results from the micro-bubbles (contrast medium).

Figure 5:
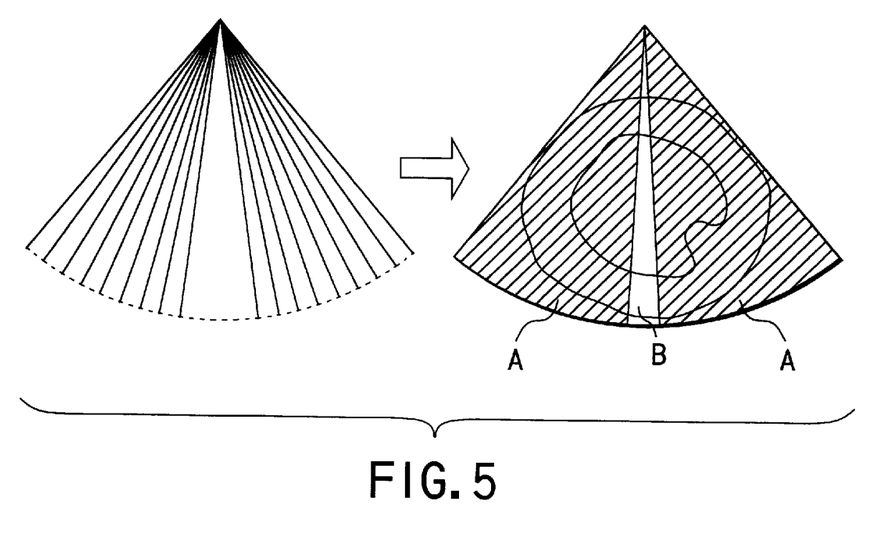
FIG. 5 is a diagram showing an image in the case where ultrasound is transmitted under the second transmission conditions according to the embodiment to extend the range where the micro-bubbles are collapsed.

The position and the space of the second ultrasound transmitting region described above are not particularly limited, so long as it is a part of the imaging region by the first ultrasound. For example, as shown in FIG. 5, contrary to the case shown in FIG. 3B, it is possible that the second ultrasound is transmitted in a larger region on both sides of the region B, instead of a smaller region A near the center of the scanning range of the first ultrasound, so that the micro-bubbles collapse in the larger region A.

The transmission of the second ultrasound in the larger region A provides the following advantages. Since the blood flows complexly in the ventriculus cordis, micro-bubbles are stirred and the concentration of the blood is comparatively constant therein. When many of the micro-bubbles are collapsed in the ventriculus cordis, the concentration is decreased.

Therefore, the first ultrasound for imaging easily reaches the posterior wall behind the ventriculus cordis. For this reason, since the posterior wall of the cardiac muscle can be imaged at high sensitivity, perfusion in the posterior wall can be detected easily. In this case, the velocity of the bloodstream in the cardiac muscle is extremely low, and therefore, the blood in the region A cannot be exchanged with that in the region B.

Figure 6:
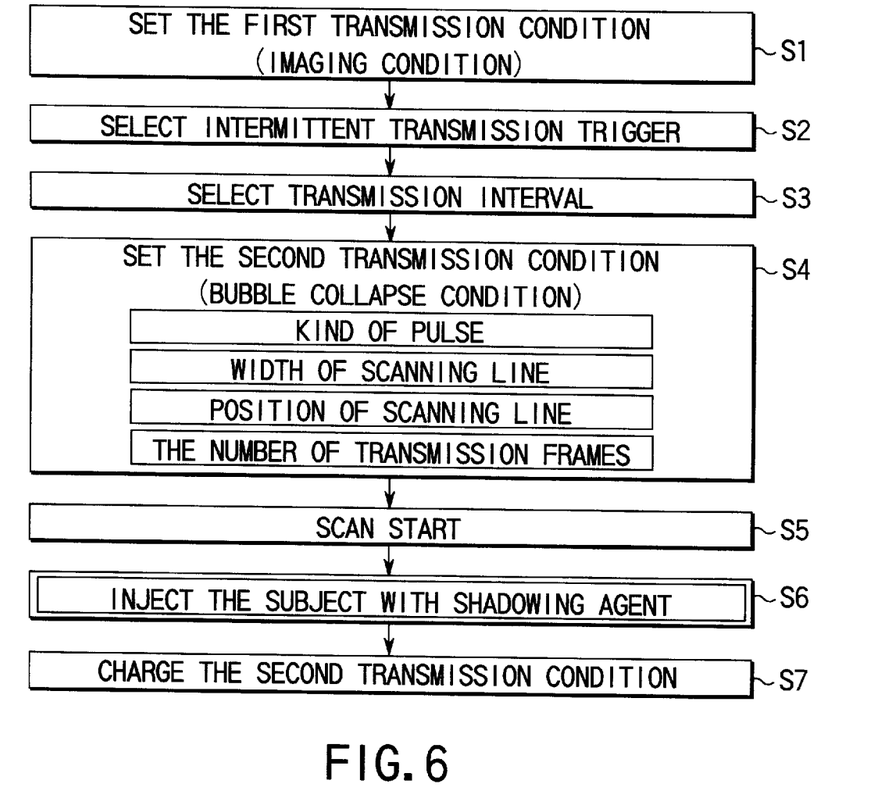
FIG. 6 is a flowchart showing operation procedures executed by the operator according to the embodiment.

Procedures executed by the operator will now be described with reference to FIG. 6.

Step 1 (S1): First, first transmission conditions relating to the first ultrasound for imaging are set.

The transmission conditions include the kind of the probe 1, the transmission sound pressure, the number of channels (transmission caliber), the transmission frequency, the burst wave number, etc.

Step 2 (S2): The operator sets whether the scanning operation by the first ultrasound for imaging is executed in synchronism with the cardiac cycle or in a fixed cycle determined by the internal clock. The scanning operation may be executed in synchronism with an external trigger other than the cardiac cycle.

Step 3 (S3): The interval t1 of the scanning operation is set in accordance with the trigger selected in Step 2. In the case where the scanning is executed in synchronism with the cardiac cycle, t1 is set to an integral number of times of the cardiac cycle. In the case where the operation is executed in a fixed cycle determined by the internal clock, t1 is set to, for example, 0.1, 0.2, . . . , 1 or 2 second.

Step 4 (S4): Then, second transmission conditions relating to the second ultrasound for collapsing micro-bubbles are set. The second transmission conditions include general conditions, such as the transmission sound pressure, and conditions characteristic of the present invention as will be described later. The second transmission conditions may be the same as the first transmission conditions, so long as the bubbles can be collapsed. However, it is preferable that at least one of the transmission sound pressure (the amplitude of the driving voltage), the number of transmission channels (transmission caliber), the transmission frequency, and the burst wave number be different from that of the first transmission conditions, so that the efficiency of collapsing the micro-bubbles can be improved. For example, the transmission frequency of the second transmission conditions is set to a value higher than that of the first transmission conditions, the transmission sound pressure of the second transmission conditions is set to a value higher than that of the first transmission conditions, and the number of transmission channels (transmission caliber) of the second transmission conditions is more (wider) than that of the first transmission conditions.

Figure 7:
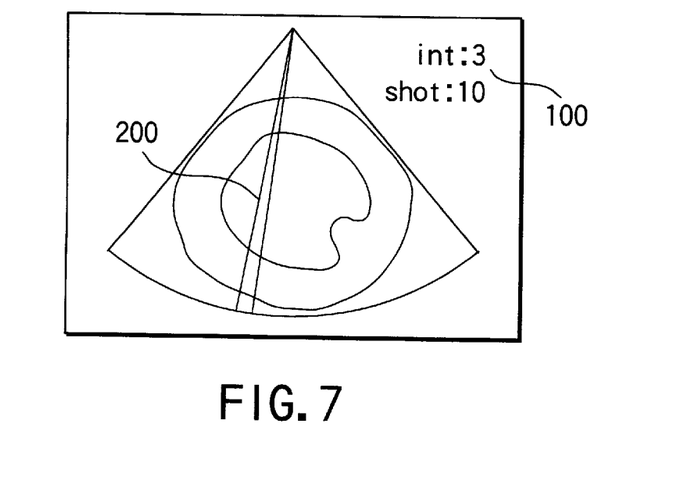
FIG. 7 is a diagram showing an example of display of the second transmission conditions.

The initial value of the width of the second ultrasound transmitting range (part of the imaging region), included in the second transmission conditions, is set by operating the input device for changing the angle of an angle marker 200 shown in FIG. 7 or inputting a numerical value of the width (number) of the ultrasound scanning lines for transmitting the second ultrasound. As will be described later, the initial value can be changed in real time, when observing, by operating the input device such as the trackball 11A.

Further, the operator selects the number of sets of transmission of the second ultrasound in the second transmission conditions, i.e., how many times the second ultrasound is transmitted (shot) to each scanning line. The number of sets can also be changed in real time, when observing, by operating the input device such as the trackball 11A. Since the second ultrasound influences an image obtained by the first ultrasound, the number of sets is particularly important.

Step 5 (S5): When the operation for setting the initial values of the second transmission conditions described above is completed, the transmission sequence as shown in FIG. 2 is started.

Step 6 (S6): Thereafter, the contrast medium (micro-bubbles) is administered to the subject and observed. In the meantime, the angle marker 200 indicating the transmission range of the second ultrasound may disturb the observation of the contrast effect. Therefore, display or non-display of the marker 200 can be selected by the console 10.

A part of the second transmission conditions is displayed in text form (e.g., interval=3 [per cardiac cycle] and the number of sets of transmission of the second ultrasound=10 in the example of FIG. 7). The second transmission conditions can also be displayed like the normal transmission conditions.

The angle marker 200 and the second transmission conditions are also displayed in the same manner in the case where image data is called and reproduced from the image memory 8 after the diagnosis.

Step 7 (S7): If necessary, the second transmission conditions set in S4 are suitably changed by means of the input devices, such as the keyboard 11B and the trackball 11A. In particular, the transmission and the stop of the second ultrasound can be switched by the input devices in real time, so that the images of the region A in both cases can be compared with each other.

Figure 8A:
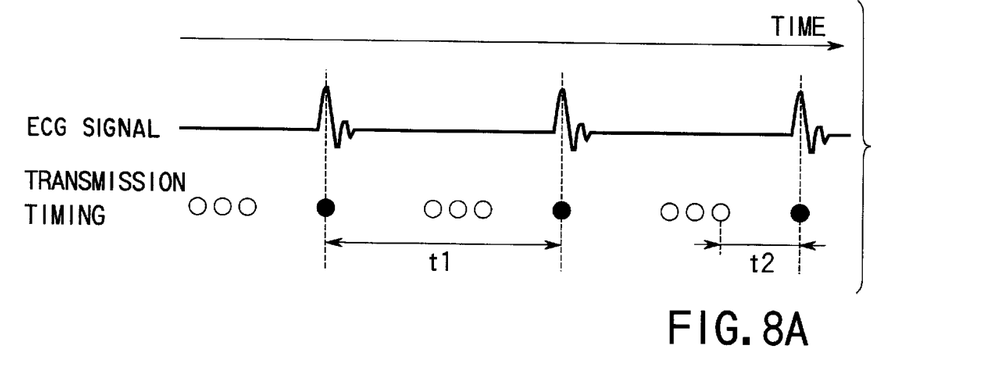
FIG. 8A is a diagram showing a transmission sequence according to a modification of the embodiment, in which the number of the second ultrasounds and the micro-bubbles inflow period t2 are changed.

In Step 4 (S4) described above, as shown in FIG. 8A, it is possible to freely set an interval t2 (micro-bubbles inflow time) between the end of transmission of the second ultrasound and the start of the scanning by the first ultrasound. It is also possible to program that the micro-bubbles inflow time t2 is changed every scanning, for example, t2–1, t2–2, t2–3, ..., t2–8=0.1, 0.2, 0.3, ..., 0.8 (sec).

Figure 9:
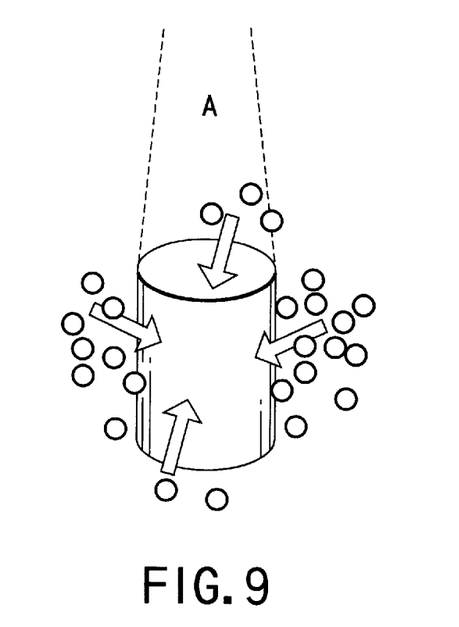
FIG. 9 is a schematic diagram showing a state of collapse and inflow of micro-bubbles according to the embodiment.

Since the micro-bubbles inflow time t2 can be set to a suitable value, the following advantages are provided. In FIG. 9, the region A is a part of all the region (cross section) scanned by the first ultrasound, in which the micro-bubble collapsing efficiency by the second ultrasound is particularly high. The longer the micro-bubbles inflow time t2, the more the new micro-bubbles flowing along with the bloodstream after the micro-bubbles are collapsed by the second ultrasound. If the micro-bubbles inflow time t2 exceed a certain lengths, the brightness level is converged (saturates).

Figure 8B:
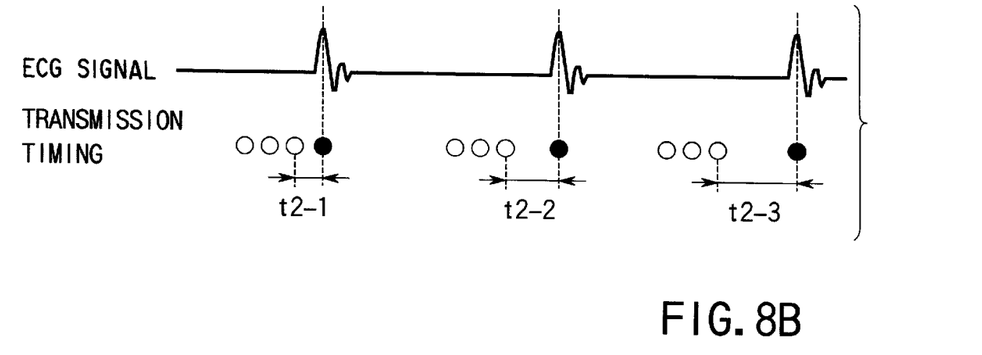
FIG. 8B is a diagram showing a transmission sequence according to another modification of the embodiment, in which the micro-bubbles inflow period t2 is programmed irregularly.
Figure 10:
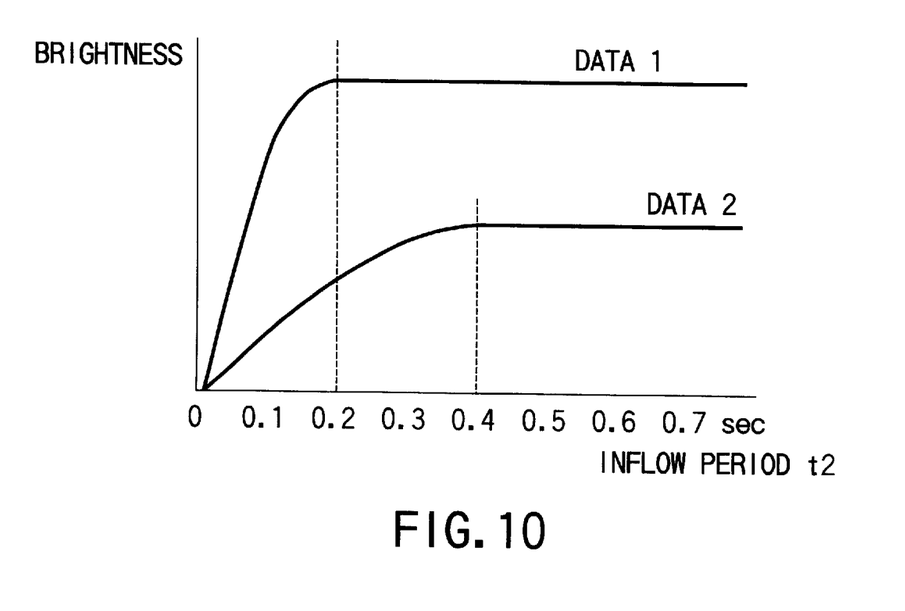
FIG. 10 is a diagram showing the correlation between a micro-bubble inflow period t2 and brightness in a micro-bubble collapse region A according to the embodiment.

FIG. 10 shows the relationship between the micro-bubbles inflow time t2 and the brightness of the region A collected by a time intensity curve (TIC) generating unit 16, when the micro-bubbles inflow time t2 is changed, as shown in FIG. 8B. The restoration time required until the brightness is restored to the saturated level after the collapse of the micro-bubbles varies depending on the site, i.e., the velocity of the bloodstream, as indicated by data 1 and data 2 shown in FIG. 10. For example, in the site represented by the data 1 where the velocity of the bloodstream is comparatively high (e.g., the heart), the restoration time is about 0.2 second. On the other hand, in the site represented by the data 2 where the velocity of the bloodstream is comparatively low (e.g., the abdominal region), the restoration time of about 0.4 second is required. Thus, the micro-bubbles inflow time t2 can be set to an optimal value in consideration of the velocity of the bloodstream in the site. Moreover, based on the convergence value of the brightness (the value of the brightness when a sufficient amount of the contrast medium is introduced), it is possible to not only obtain information that the capacity of the blood is higher in the site of data 1 than that of data 2, but also calculate quantitatively the velocity of the bloodstream to the region of interest in the tissue of the internal organs or the bloodstream capacity.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
    an ultrasound probe;
    a transmitting device for driving the ultrasound probe to transmit ultrasound to a subject injected with micro-bubbles;
    a transmission control circuit for controlling the transmitting device to scan throughout an imaging region of the subject with ultrasound for imaging during a scanning operation, the scanning operation being repeated, and ultrasound for collapsing the micro-bubbles being transmitted in an interval between scanning operations;
    a receiving device for receiving echoes reflected by the subject during the scanning operation through the ultrasound probe;
    a unit for producing image data relating to the imaging region based on the received echoes; and
    a processor for generating a curve representing correlation between an interval from an end of transmission of the ultrasound for collapsing the micro-bubbles to a start of the scanning operation and brightness of a place where the ultrasound for collapsing the micro-bubbles is transmitted;
    wherein an interval from the end of transmission of the ultrasound for collapsing the micro-bubbles to the start of the scanning operation is changed in every scanning operation.

2. An ultrasonic diagnostic apparatus according to claim 1, wherein the ultrasound for collapsing the micro-bubbles is transmitted to a part of the imaging region.

3. An ultrasonic diagnostic apparatus according to claim 1, wherein the scanning operation is intermittently repeated in synchronism with a cardiographic waveform.

4. An ultrasonic diagnostic apparatus according to claim 1, wherein the scanning operation is intermittently repeated in an arbitrary cycle.

5. An ultrasonic diagnostic apparatus according to claim 1, wherein the ultrasound for collapsing the micro-bubbles is repeatedly transmitted in one direction in each interval between the scanning operations.

6. An ultrasonic diagnostic apparatus according to claim 1, wherein the ultrasound for imaging is transmitted under transmission conditions in which at least one of a transmission sound pressure, a transmission caliber, a transmission frequency and a burst wave number, is different from that of the ultrasound for collapsing the micro-bubbles.

7. An ultrasonic diagnostic apparatus according to claim 1, wherein the ultrasound for collapsing the micro-bubbles has a higher transmission sound pressure, a wider transmission caliber, a lower transmission frequency, and/or a more burst wave number than that of the ultrasound for imaging.

8. An ultrasonic diagnostic apparatus according to claim 1, wherein transmission conditions of the ultrasound for collapsing the micro-bubbles are arbitrarily set in accordance with operator's instructions.

9. An ultrasonic diagnostic apparatus according to claim 1, wherein delay data for determining a transmission direction of the ultrasound for collapsing the micro-bubbles is same as part of delay data used to oscillate the ultrasound for imaging.

10. An ultrasonic diagnostic apparatus according to claim 1, wherein delay data for determining a transmission direction of the ultrasound for collapsing the micro-bubbles is different from delay data used to oscillate the ultrasound for imaging.

11. An ultrasonic diagnostic apparatus according to claim 1, wherein at least one of a transmission range and a transmission direction of the ultrasound for collapsing the micro-bubbles is arbitrarily set in accordance with operator's instructions.

12. An ultrasonic diagnostic apparatus according to claim 1, wherein at least one of a transmission range and a transmission direction of the ultrasound for collapsing the micro-bubbles can be changed in accordance with operator's instructions during the scanning operation.

13. An ultrasonic diagnostic apparatus according to claim 1, wherein the transmission of the ultrasound for collapsing the micro-bubbles can be ceased in accordance with operator's instructions during the scanning operation.

14. An ultrasonic diagnostic apparatus according to claim 1, wherein transmission conditions of the ultrasound for collapsing the micro-bubbles are displayed on a screen along with the image data.

15. An ultrasonic diagnostic apparatus according to claim 1, wherein a marker indicating a transmission range of the ultrasound for collapsing the micro-bubbles is superimposed on the image data.

16. An ultrasonic diagnostic apparatus according to claim 15, wherein the marker can be erased in accordance with operator's instructions.

17. An ultrasonic diagnostic apparatus according to claim 15, wherein an interval between an end of transmission of the ultrasound for collapsing the micro-bubbles and a start of the scanning operation can be adjusted in accordance with operator's instructions.

18. An ultrasonic diagnostic apparatus comprising:

an ultrasound probe;

a transmitting device for driving the ultrasound probe to transmit ultrasound to a subject injected with micro-bubbles as ultrasound reflectors having high reflectivity;

a receiving device for receiving echoes reflected by the subject through the ultrasound probe;

a unit for producing image data based on the received echoes;

a transmission control circuit for controlling the transmitting device to make a first ultrasound transmission for forming an image of a ventricle and cardiac muscle and a second ultrasound transmission for collapsing micro-bubbles in a part of the ventricle and cardiac muscle in the image repeatedly, the transmitting conditions of first ultrasound transmission are suitable for image forming of the ventricle and cardiac muscle with micro-bubble, the transmitting conditions of second ultrasound transmission are more suitable for collapsing micro-bubble s a s compared to the transmitting conditions of the first ultrasound transmission; and a processor for generating a curve representing correlation between an interval from an end of transmission of the ultrasound for collapsing the micro-bubbles to a start of the scanning operation and brightness of a place where the ultrasound for collapsing the micro-bubbles is transmitted.

19. An ultrasonic diagnostic apparatus comprising:

an ultrasound probe;

a transmitting device for driving the ultrasound probe to transmit ultrasound to a subject injected with micro-bubbles as ultrasound reflectors having high reflectivity;

a receiving device for receiving echoes reflected by the subject through the ultrasound probe;

a unit for producing image data based on the received echoes;

a transmission control circuit for controlling the transmitting device to make a first ultrasound transmission for forming an image of a liver and a second ultrasound transmission for collapsing micro-bubbles in part of the liver in the image repeatedly, the transmitting conditions of first ultrasound transmission are suitable for image forming of the liver with micro-bubble, the transmitting conditions of second ultrasound transmission are more suitable for collapsing micro-bubbles as compared to the transmitting conditions of the first ultrasound transmission; and a processor for generating a curve representing correlation between an interval from an end of transmission of the ultrasound for collapsing the micro-bubbles to a start of the scanning operation and brightness of a place where the ultrasound for collapsing the micro-bubbles is transmitted.

* * * * *